United States Patent [19]
Osborn, III et al.

[11] Patent Number: 5,846,230
[45] Date of Patent: *Dec. 8, 1998

[54] ABSORBENT ARTICLE WITH MEANS FOR DIRECTIONAL FLUID DISTRIBUTION

[75] Inventors: Thomas Ward Osborn, III, Cincinnati; Deborah Catherine Schmitz, West Chester; James William Cree; Melisse Noel Elder, both of Cincinnati, all of Ohio

[73] Assignee: The Procter & Gamble Co., Cincinnati, Ohio

[ * ] Notice: The term of this patent shall not extend beyond the expiration date of Pat. No. 5,647,862.

[21] Appl. No.: 886,831

[22] Filed: Jul. 1, 1997

Related U.S. Application Data

[63] Continuation of Ser. No. 513,600, Aug. 10, 1995, Pat. No. 5,647,862, which is a continuation of Ser. No. 340,013, Nov. 15, 1994, which is a continuation of Ser. No. 83,425, Jun. 28, 1993.

[51] Int. Cl.$^6$ ..................................................... A61F 13/15
[52] U.S. Cl. .......................................... 604/378; 607/387
[58] Field of Search .................................. 604/378, 387, 604/885.1

[56] References Cited

U.S. PATENT DOCUMENTS

| | | |
|---|---|---|
| H1511 | 12/1995 | Chappell et al. . |
| 810,119 | 1/1906 | Green . |
| 3,559,649 | 2/1971 | Grad et al. . |
| 3,736,931 | 6/1973 | Glassman . |
| 3,768,480 | 10/1973 | Mesek et al. . |
| 3,903,890 | 9/1975 | Mesek et al. . |
| 3,954,107 | 5/1976 | Chesky et al. . |
| 4,029,101 | 6/1977 | Chesky et al. . |
| 4,195,634 | 4/1980 | DiSalvo et al. . |
| 4,333,462 | 6/1982 | Holtman et al. . |
| 4,531,945 | 7/1985 | Allison . |
| 4,559,051 | 12/1985 | Hanson . |
| 4,624,666 | 11/1986 | DeRossett et al. . |
| 4,643,727 | 2/1987 | Rosenbaum . |
| 4,678,464 | 7/1987 | Holtman . |
| 4,723,953 | 2/1988 | Rosenbaum et al. . |
| 4,795,453 | 1/1989 | Wolfe . |
| 4,798,603 | 1/1989 | Meyer et al. . |
| 4,908,026 | 3/1990 | Sukiennik et al. . |
| 4,963,139 | 10/1990 | Dabroski . |
| 4,973,325 | 11/1990 | Sherrod et al. . |
| 4,988,344 | 1/1991 | Reising et al. . |
| 4,988,345 | 1/1991 | Reising . |
| 5,037,412 | 8/1991 | Tanzer et al. . |
| 5,171,302 | 12/1992 | Buell . |
| 5,197,959 | 3/1993 | Buell . |
| 5,219,341 | 6/1993 | Serbiak et al. . |
| 5,248,309 | 9/1993 | Serbiak et al. . |
| 5,647,862 | 7/1997 | Osborn, III et al. . |

FOREIGN PATENT DOCUMENTS

| | | |
|---|---|---|
| 0 523 683 A1 | 1/1993 | European Pat. Off. . |
| 0 534 488 A1 | 3/1993 | European Pat. Off. . |
| 0 572 033 A2 | 12/1993 | European Pat. Off. . |
| WO 93/01780 | 2/1993 | WIPO . |
| WO 93/09744 | 5/1993 | WIPO . |
| WO 93/09745 | 5/1993 | WIPO . |
| WO 93/11727 | 6/1993 | WIPO . |

*Primary Examiner*—Robert A. Clarke
*Attorney, Agent, or Firm*—Jeffrey V. Bamber; Steven W. Miller; Jacobus C. Rasser

[57] ABSTRACT

An absorbent article, such as a generally thin, flexible sanitary napkin with a topsheet, backsheet and absorbent core is provided. The absorbent article has a means for directional fluid distribution such as a fluid directing strip positioned between the topsheet and absorbent core, and an absorbent strip positioned between the topsheet and fluid directing strip. The relationships between the sizes of the fluid directing strip and the absorbent strip are such that the width of the fluid directing strip is greater than that of the absorbent strip and the length of the absorbent strip in greater than that of the fluid directing strip, so that bodily exudates may be directed toward the ends of the absorbent core even when the sanitary napkin assumes a body-conforming shape or is otherwise distorted during use.

20 Claims, 4 Drawing Sheets

ABSORBENT ARTICLE WITH MEANS FOR DIRECTIONAL FLUID DISTRIBUTION

This is a continuation of application Ser. No. 08/513,600, filed on Aug. 10, 1995 now U.S. Pat. No. 5,647,862, which is a continuation of application Ser. No. 08/340,013, filed on Nov. 15, 1994; which is a continuation of application Ser. No. 08/083,425, filed on Jun. 28, 1993.

FIELD OF THE INVENTION

The present invention relates to absorbent articles, particularly sanitary napkins. More particularly, the present invention relates to a generally thin, flexible sanitary napkin with a means for directional fluid distribution.

BACKGROUND OF THE INVENTION

Absorbent articles, such as sanitary napkins, panty liners, and incontinence pads that are designed to absorb and retain liquids and other discharges from the human body and to prevent body and clothing soiling, having various different constructions are well known.

The current tendency has been to develop absorbent articles such as sanitary napkins which are increasingly thinner and conform better to the body. Recently, efforts have been directed to developing thinner sanitary napkins which have the capacity to absorb and contain medium to high menstrual discharges. Previously, such discharges could only be handled by relatively thick sanitary napkins. Examples of thin sanitary napkins having capacities great enough to handle medium to high menstrual flows are disclosed in U.S. Pat. Nos. 4,950,264 and 5,009,653, issued to Osborn, on Aug. 21, 1990 and Apr. 23, 1991, respectively.

One of the main objectives in developing absorbent articles is to utilize the entire capacity of the absorbent article. The utilization of the capacity for absorption of menses and other bodily exudates in the thin sanitary napkins described in the Osborn references is achieved at least in part by the presence of a "wipe acquisition sheet" that distributes the exudates more evenly over the underlying absorbent core. In general, products that are not provided with a structure like the wipe acquisition sheet described in the aforementioned patents, typically distribute liquids in a circular pattern, resulting in liquids reaching the longitudinal side edges of the absorbent article before the end regions of the absorbent article are utilized. When liquids come near the longitudinal side edges of the absorbent article, the chance for leakage from the sides of the product increases, despite available absorbent capacity in the end regions of the absorbent article.

In the past, a number of efforts have been made to direct exudates in an attempt to utilize more of the absorbent capacity of an absorbent article. A number of these efforts have used absorbent means or densification of absorbent means. Some of such efforts are described in U.S. Pat. No. 4,678,453 issued Jul. 7,1987 to Holtman and U.S. Pat. No. 4,624,666 issued Nov. 25, 1986 to DeRossett, et al. Absorbent articles which use absorbent means to direct fluid flow, however, are typically subject to the disadvantage that the absorbent means will tend to become saturated and interfere with its fluid directing capabilities.

Another series of patents teaches the use of baffles, barriers, and transfer members for liquid transport. For instance, U.S. Pat. 4,029,101 issued Jun. 14, 1977 to Chesky et al. discloses using an elongated baffle near the base of the pad. U.S. Pat. No. 3,736,931 issued Jun. 5, 1973 to Glassman discloses using a moisture impervious layer in the pad. However, in both of these examples, liquids may wick laterally before reaching the baffle or the moisture impervious layer. This may tend to cause side failure (or side leakage), particularly when the pad bunches during wear. In such cases, the barrier or transfer member may be disturbed by the bunching of the pad, and body fluids may circumvent the barrier or transfer member and flow directly toward the longitudinal side edges of the product.

Thus, a need exists for an absorbent article, such as a sanitary napkin that has an improved means for directional fluid distribution that distributes bodily exudates so that the exudates will not reach the longitudinal side edges of the absorbent article before reaching the end regions of the article.

It is, therefore, an object of the present invention to provide an absorbent article such as a sanitary napkin with a means for enabling the entire absorbent capacity of the sanitary napkin to be utilized before liquids reach the longitudinal side edges of the napkin.

It is another object of the present invention to provide a generally thin, flexible sanitary napkin that conforms to the wearer's body.

SUMMARY OF THE INVENTION

The present invention is directed to an absorbent article, such as a sanitary napkin. More preferably, the present invention is directed to a generally thin, flexible sanitary napkin with a means for directional fluid distribution.

The sanitary napkin of the present invention has a longitudinal centerline, a transverse centerline, a body-facing surface, and a garment-facing surface. The sanitary napkin comprises a liquid pervious topsheet, a liquid impervious backsheet joined to the topsheet, an absorbent core positioned between the topsheet and backsheet, and a means for directional fluid distribution. The means for directional fluid distribution can, in one embodiment, comprise a liquid impervious or semi-pervious fluid directing strip positioned between the absorbent core and the topsheet and a liquid transporting structure such as an absorbent strip positioned between the fluid directing strip and the topsheet. The width of the absorbent strip is preferably less than the width of the fluid directing strip. The length of the absorbent strip is preferably greater than or equal to the length of the fluid directing strip so that it is capable of wicking liquids over the fluid directing strip toward the ends of the core.

There are a non-limiting number of embodiments of the means for directional fluid distribution. In one embodiment, the fluid directing strip comprises a hydrophobic file such as a polyethylene film. The fluid directing strip in this embodiment may be apertured or non-apertured. In another embodiment, the absorbent strip and the fluid directing strip can be replaced by a single component which serves the function of both strips. In other embodiments, the fluid directing strip may have a plurality of longitudinally-oriented channels formed therein. In another embodiment, the fluid directing strip can be comprised of a hydrophobic structure, such as a film which has a hydrophilic component dispersed thereon. The hydrophobic portion provides a bucket-like structure that has to be filled up before overflowing to the hydrophilic portion of the fluid directing strip. In still other embodiments, the fluid directing strip may comprise a structure such as a plastic film that has a plurality of troughs formed therein.

The sanitary napkin preferably has a caliper less than or equal to about 4 millimeters and is flexible enough to conform to the wearer's body. The components of the means for directional fluid distribution are sufficiently flexible and joined in such a way that they maintain the desired relationships with each other during wear, particularly when the sanitary napkin is laterally compressed. The sanitary napkin in different embodiments may be predisposed to bend so that it assumes a "W"-shaped cross-section, an inverted "V"-shaped cross-section, or other suitable cross-sectional configuration when worn.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

DETAILED DESCRIPTION OF PREFERRED EMBODIMENTS

1. General Characteristics of the Absorbent Article

Figure 1:
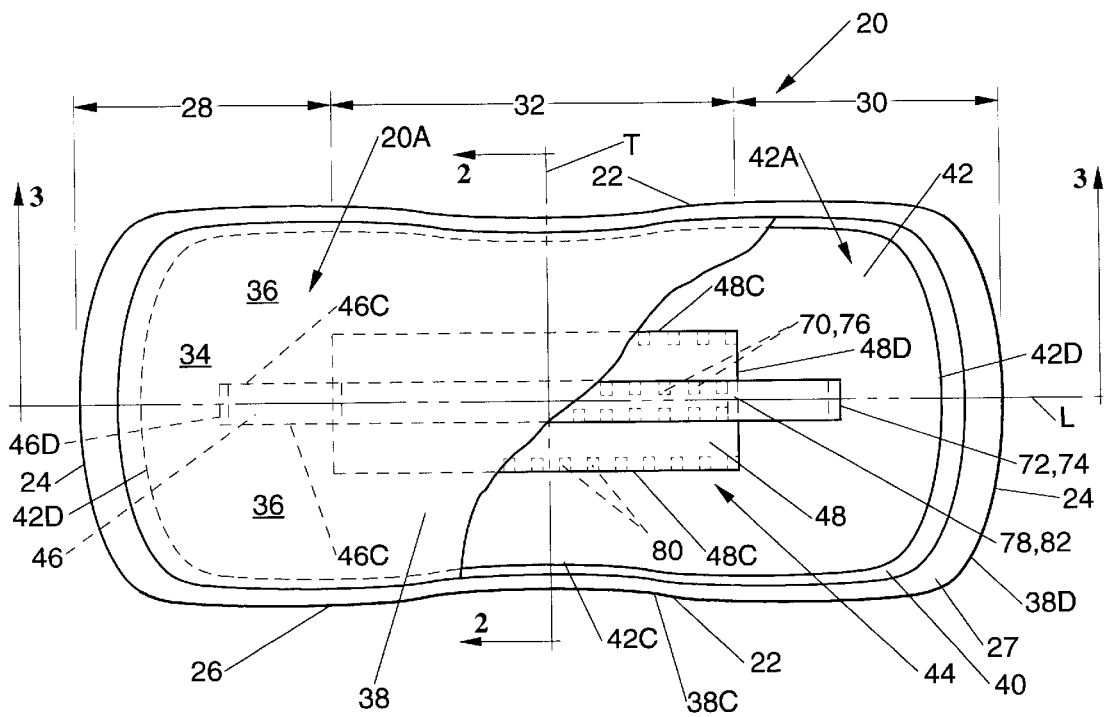
FIG. 1 is a top plan view of a preferred sanitary napkin embodiment of the present invention shown with a portion of the topsheet removed to show the underlying means for directional fluid distribution.

FIG. 1 shows a particularly preferred embodiment of the disposable absorbent article of the present invention, sanitary napkin 20.

The term "absorbent articles", as used herein, refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner).

The term "sanitary napkin", as used herein, refers to an absorbent article which is worn by females adjacent to the pudendal region, generally external to the urogenital region, and which is intended to absorb and contain menstrual fluids and other vaginal discharges from the wearer's body (e.g., blood, menses, and urine). It should be understood, however, that the present invention is also applicable to other feminine hygiene or catamenial pads such as panty liners, or other absorbent articles such as incontinence pads, and the like.

The sanitary napkin 20 has two surfaces, a body-contacting surface or "body surface" 20A and a garment surface 20B. The sanitary napkin 20 is shown in FIG. 1 as viewed from its body surface 20A. The body surface 20A is intended to be worn adjacent to the body of the wearer while the garment surface 20B is on the opposite side and is intended to be placed adjacent to the wearer's undergarments when the sanitary napkin 20 is worn.

The sanitary napkin 20 has two centerlines, a longitudinal centerline L and a transverse centerline T. The terms "longitudinal" and "transverse" are defined in U.S. Pat. No. 5,007,906 entitled "Decoupled Sanitary Napkin", issued to Osborn, et al. on Apr. 16, 1991. (The term "lateral" is used herein interchangeably with the term "transverse".) The sanitary napkin 20 has a longitudinal dimension or length that runs in the general direction of the longitudinal centerline L, and a (typically shorter) transverse dimension or width that runs in the general direction of the transverse centerline T.

The sanitary napkin 20 has a periphery 26 which is defined by the outer edges of the sanitary napkin 20 in which the longitudinal edges (or "side edges") are designated 22 and the end edges (or "ends") are designated 24, and the corners of the sanitary napkin are designated 27. The sanitary napkin has two end regions, which are designated first end region 28 and second end region 30. A central region 32 is disposed between the end regions 28 and 30. The end regions 28 and 30 extend outwardly from the edges of the central region 32 about ⅛ to about ⅓ of the length of the sanitary napkin. A detailed description of the central region 32 and the two end regions 28 and 30 is contained in U.S. Pat. No. 4,690,680 issued to Higgins on Sep. 1, 1987.

Figure 2:
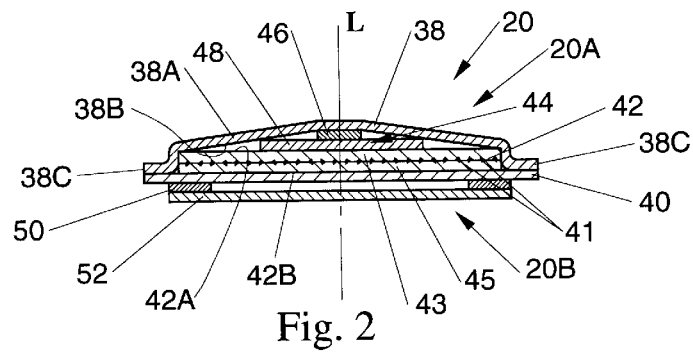
FIG. 2 is an enlarged cross-sectional view of the preferred sanitary napkin embodiment shown in FIG. 1 taken along line 2—2 of FIG. 1.

FIG. 2 shows that the sanitary napkin 20 preferably comprises a liquid pervious topsheet 38, a liquid impervious backsheet 40, an absorbent core 42 positioned between the topsheet 38 and backsheet 40, and a means for directional fluid distribution (or means for directional liquid distribution) 44 positioned between the topsheet 38 and the absorbent core 42. The means for directional fluid distribution 44 shown In FIGS. 1 and 2 comprises a liquid transporting component such as an absorbent strip 46 positioned between the topsheet 38 and the absorbent core 42, and a liquid directing component such as a liquid impervious fluid directing strip 48 positioned between absorbent strip 46 and the absorbent core 42.

2. The Individual Components of the Sanitary Napkin

A. The Topsheet

Examining the components of the sanitary napkin in more detail with continuing reference to FIGS. 1 and 2, the topsheet 38 is the component which is oriented towards and contacts the body of the wearer, and receives bodily discharges.

The topsheet 38 is liquid pervious and should be flexible and non-irritating to the skin. As used herein the term "flexible" and refers to materials which are compliant and readily conform to the shape of the body or respond by easily deforming in the presence of external forces. The topsheet 38 should exhibit good strikethrough and low rewet characteristics, permitting bodily discharges to rapidly penetrate the thickness of the topsheet 38 and move into the absorbent strip 46 and sequentially into the absorbent core 42, but not flow back through the topsheet 38 to the skin of the wearer. Preferably, the topsheet 38 is not noisy, to provide discretion for the wearer. The topsheet 38 should be sanitary, clean in appearance and somewhat opaque to hide bodily discharges collected in and absorbed by the absorbent strip 46 and absorbent core 42.

FIG. 2 shows that the topsheet 38 has two sides (or faces or surfaces), including a body-facing side 38A and a garment-facing side (or core-facing side) 38B. The body-facing side 38A of the topsheet 38 generally forms at least a portion of the body-contacting surface ("body surface") 20A of the sanitary napkin 20. The topsheet 38 has, as shown in FIG. 1, two longitudinal edges 38C and two end edges 38D.

(A similar numbering system can be used for the other components of the sanitary napkin. That is, the side of the component facing the wearer's body can be designated by the number of the component and a reference letter "A". The side of the component facing the wearer's undergarments can be designated by the number of the component and the letter "B". The side and end edges can be designated by the number of the component and the reference letters "C" and "D", respectively.)

A suitable topsheet 38 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers), or from a combination of natural and synthetic fibers.

A preferred topsheet 38 comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer.

Suitable formed films are described in U.S. Pat. No. 3,929,135, issued to Thompson on Dec. 30, 1975; U.S. Pat. No. 4,324,246 issued to Mullane, et al. on Apr. 13, 1982; U.S. Pat. No. 4,342,314 issued to Radel. et al. on Aug. 3, 1982; U.S. Pat. No. 4,463,045 issued to Ahr et al. on Jul. 31, 1984; U.S. Pat. No. 4,629,643 issued to Curro, et al. on Dec. 16, 1986; and U.S. Pat. No. 5,006,394 issued to Baird on Apr. 9, 1991. The preferred topsheet for the present invention is the formed film described in one or more of the above patents and marketed on sanitary napkins by The Procter & Gamble Company as "DRI-WEAVE".

The topsheet 38 has a plurality of apertures to permit liquids deposited thereon to pass through to the core 42. An apertured polyolefinic film topsheet 38 having about 5 to about 60 percent open area, typically about 25 percent open area, and a thickness of about 0.01 to about 0.05 millimeters prior to aperturing and about 0.42 to about 0.51 millimeters after aperturing is suitable. A particularly suitable topsheet 38 may be made in accordance with U.S. Pat. No. 4,342,314 issued Aug. 3, 1982 to Radel et al. and U.S. Pat. No. 4,463,045 issued Jul. 31, 1984 to Ahr, et al. A topsheet 38 made of model X-3265 or model P1552 apertured formed film sold by Tredegar Corporation of Terre Haute, Ind. has been found to work well.

Preferably, the topsheet 38 is sprayed or otherwise treated with a surfactant to enhance liquid penetration to the absorbent strip 46 and underlying absorbent core 42. Suitable methods for treating the topsheet with a surfactant are described in U.S. Pat. Nos. 4,950,264 and 5,009,653 issued to Osborn. The surfactant is typically nonionic and should be non-irritating to the skin. A surfactant density of about 0.01 milligrams per square centimeter of topsheet 38 area is suitable. A suitable surfactant is sold by Glyco Chemical, Inc. of Greenwich, Conn. as Pegosperse 200 ML.

B. The Absorbent Core

The absorbent core 42 is one of the means for collecting and containing bodily discharges, particularly menses, deposited thereon or which otherwise traverse through the liquid permeable topsheet 38.

The absorbent core 42 may be manufactured in a wide variety of sizes and shapes (e.g., rectangular, oval, hourglass, dog bone, asymmetric, etc.). The absorbent core 42 has a body surface 42A, a garment surface 42B, side edges 42C, and end edges 42D. The core 42 is preferably conformable and non-irritating to the skin. The absorbent core 42 of the preferred sanitary napkin 20 shown in FIGS. 1–3 comprises a modified hourglass-shaped laminate comprising two layers of tissue, upper layer 43 and lower layer 45 with absorbent gelling material particles 41 sandwiched between the tissue layers. The absorbent core 42 can, in other embodiments, be made of a number of other suitable materials.

Suitable materials for the absorbent core 42 include but are not limited to: comminuted wood pulp which is generally referred to as airfelt; creped cellulose wadding; tissue including tissue wraps and tissue laminates; synthetic fibers, especially polymeric fibers, such as crimped polyester fibers; meltblown polymers including coform; chemically stiffened, modified or cross-linked cellulosic fibers; fibers have intra-fiber capillary channels preferably on their exterior surfaces (capillary channel fibers); peat moss; absorbent foams; absorbent sponges; superabsorbent hydrogel-forming polymeric gelling agents; or any equivalent materials or combination of materials, or mixtures of these materials.

Polymeric gelling agents are particularly preferred absorbent materials for use in the absorbent core 42. Polymeric gelling agents are those materials which, upon contact with fluids (i.e., liquids) such as water or body fluids, imbibe such fluids and thereby form hydrogels. In this manner, fluid discharged into the absorbent core 42 can be acquired and held by the polymeric gelling agent, thereby providing the absorbent articles described herein with enhanced absorbent capacity and/or improved fluid retention performance. Suitable absorbent gelling materials are described in U.S. Pat. No. Re. 32,649 issued Apr. 19, 1988 to Brandt et al. and U.S. Pat. No. 5,102,597 issued to Roe, et al. on Apr. 7, 1992. A suitable laminate of absorbent gelling materials and tissue may be purchased from Grain Processing Corporation of Muscatine, Iowa under Model Number L535.

Suitable cross-linked cellulose fibers for the absorbent core are described in U.S. Pat. No. 4,888,093, issued Dec. 19, 1989 to Cook, et al.; U.S. Pat. No. 4,822,543, issued Apr. 18, 1989 to Dean, et al.; U.S. Pat. No. 4,889,595, issued Dec. 26, 1989 to Schoggen, et al.; U.S. Pat. No. 4,898,642, issued Feb. 6, 1990 to Moore, et al.; U.S. Pat. No. 4,935,022 issued Jun. 19, 1990 to Lash et al.; and, U.S. Pat. No. 5,183,707 issued Feb. 2, 1993 to Herron, et al.; U.S. Pat. No. 5,217,445 issued Jun. 8, 1993 to Young, et al.; in EPO Patent Application Publication Nos. 0 427 316 A2 and 0 427 317 A2 published in the name of Herron, et al. on May 15, 1991; and in EPO Patent Application Publication No. 0 429 112 A2 published in the name of Herron, et al. on May 29, 1991.

Capillary channel fibers are described in the following patent applications which were filed on Jul. 23, 1991: U.S. patent application Ser. No. 07/724,404 filed in the names of Thompson, et al. and U.S. patent application Ser. No. 07/734,392 filed in the names of Thompson, et al. (combined in PCT Publication No. WO 93/01779 published Feb. 4, 1993); and in U.S. patent application Ser. No. 07/734,405 filed in the names of Buenger, et al. (PCT Publication No. WO 93/02251 published Feb. 4, 1993). These patent applications may be referred to collectively as the "Capillary Channel Fiber" patent applications. Suitable capillary channel fibers are also described in PCT International Patent Publication No. WO 92/00407 and PCT Publication No. WO 93/02235 published in the Phillips, et al. on Feb. 4, 1993 and assigned to Eastman Kodak Company, and in U.S. Pat. No. 5,200,248 issued to Thompson, et al. on Apr. 6, 1993. Suitable capillary channel fibers are those designated SW173 available from Eastman Chemical Company.

Suitable foam materials are described in U.S. Pat. No. 5,147,345 entitled "High Efficiency Absorbent Articles for Incontinence Mangagement" issued to Young, et al. on Sep. 15, 1992, U.S. Pat. No. 5,198,472 entitled "Process for Preparing Emulsions That are Polymerizable to Absorbent Foam Materials" issued to DesMarais, et al. on Mar. 30, 1993 and in PCT Publication No. WO 93/04113 entitled "Method for Hydrophilizing Absorbent Foam Materials" published in the name of DesMarais on Mar. 4, 1993.

The configuration and construction of the absorbent core 42 may be varied (e.g., the absorbent core may have: varying caliper zones, for example, the core may be profiled so as to be thicker in the center; hydrophilic gradients; superabsorbent gradients; or lower density and lower average basis weight acquisition zones; or it may comprise one or more layers or structures). The total absorbent capacity of the absorbent core 42 should, however, be compatible with the design loading and the intended use of the sanitary napkin 20. Further, the size and absorbent capacity of the absorbent core 42 may be varied to accommodate different uses such as incontinence pads, pantiliners, regular sanitary napkins, or overnight sanitary napkins.

Some examples of absorbent structures that can be used as the absorbent core in the sanitary napkin of the present invention are described in U.S. Pat. No. 4,578,068 entitled "Absorbent Laminate Structure" issued to Kramer, et al. on Mar. 25, 1986; U.S. Pat. No. 4,640,810 entitled "System for Producing an Airlaid Web" issued to Laursen, et al. Feb. 3, 1987 (or airlaid structures made by different processes); U.S. Pat. Nos. 4,950,264 and 5,009,653 entitled "Thin, Flexible Sanitary Napkin" issued to Osborn on Aug. 21, 1990 and Apr. 23, 1991; U.S. Pat. No. 4,610,678 entitled "High-Density Absorbent Structures" issued to Weisman et al. on Sep. 9, 1986; U.S. Pat. No. 4,834,735 entitled "High Density Absorbent Members Having Lower Density and Lower Basis Weight Acquisition Zones", issued to Alemany et al. on May 30, 1989; European Patent Application No. 0 198 683, published Oct. 22, 1986 in the name of Duenk, et al.; and in U.S. patent application Ser. No. 07/810,774 and its continuation-in-part, Ser. No. 07/944,764 both entitled "Absorbent Article Having Fused Layers" filed in the name of Cree, et al. on Dec. 17, 1991 and Sep. 14, 1992, respectively.

C. The Means for Directional Fluid Distribution

Figure 3:
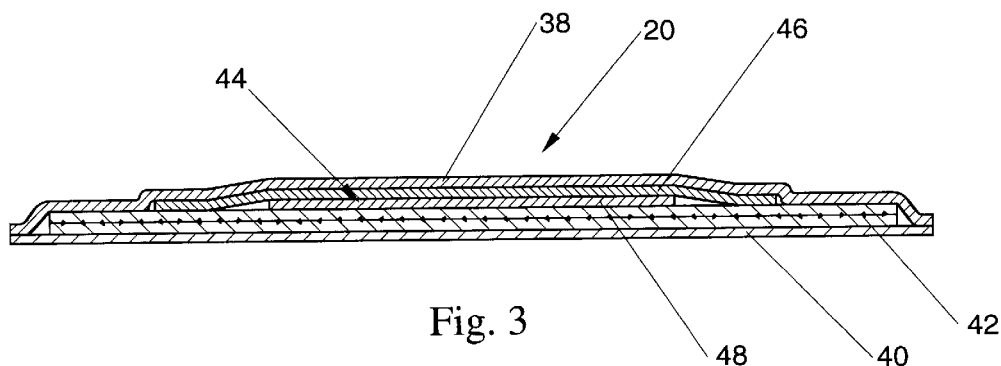
FIG. 3 is a cross-sectional view of the preferred sanitary napkin embodiment shown in FIG. 1 taken along line 3—3.

The means for directional fluid distribution 44, as shown in FIGS. 1–3, is positioned between the topsheet 38 and absorbent core 42. The means for directional fluid distribution is intended to preferentially distribute bodily exudates toward the ends of the sanitary napkin. The exudates are preferably distributed so that exudates will not reach the longitudinal side edges of the sanitary napkin at least until exudates are transported so as to substantially use any available absorbent capacity in the end regions of the absorbent core of the sanitary napkin.

The means for directional fluid distribution 44 is preferably centered along the longitudinal centerline of the sanitary napkin. The means for directional fluid distribution 44 can also either be centered along the transverse centerline, or it can be offset from the transverse centerline (that is, positioned forward or rearward of the transverse centerline). If the means for directional fluid distribution 44 is offset from the transverse centerline, it is preferably positioned so that it at least partially lies in the central region 32 of the sanitary napkin 20.

The means for directional fluid distribution 44 comprises: (1) a liquid transporting component such as an absorbent strip 46 positioned between the topsheet 38 and the absorbent core 42, and (2) a fluid directing component (i.e., a liquid directing component) such as a liquid impervious fluid directing strip 48 positioned between absorbent strip 46 and the absorbent core 42.

(1) the Liquid Transporting Component

The liquid transporting component, absorbent strip 46, is intended to collect bodily discharges, particularly senses, deposited thereon or which otherwise traverse through the topsheet 38 and transport these bodily discharges to the underlying fluid directing strip 48 and toward the ends 420 of the absorbent core 42. The absorbent strip 46 can also be used to draw some of these bodily discharges away from the topsheet 38 and absorb some of such discharges.

The absorbent strip 46 shown in FIG. 1 is a rectangular strip that has dimensions that are narrower in width and longer in length than the fluid directing strip 48 (described below). The dimensions of the absorbent strip 46 can vary between certain limits. The preferred dimensions range from between about 0.4–0.5 inches (about 1 cm.) and about 1.75 inches (about 4–4.4 cm.) in width and between about 2.75 inches (about 7 cm.) and about 6 inches (about 15 cm.) in length. The dimensions can, however, be less than or greater than these preferred dimensions as long as the relationship between the sizes and boundaries of the absorbent strip, the fluid directing strip, and the absorbent core described herein are maintained.

The absorbent strip 46 is preferably conformable and nonirritating to the skin. Suitable materials for the absorbent strip 46 include, but are not limited to any of those materials used in the absorbent core such as tissue paper, creped cellulose wadding, cross-linked cellulose fibers, capillary channel fibers, absorbent foams, synthetic staple fibers, polymeric fibers, superabsorbent hydrogel-forming polymer gelling agents in particle or fibrous form or as laminates, peat moss, or any equivalent materials or combination of materials.

The terms "strip" and "layer", as used herein, are not limited to single unfolded sheets. These terms are also intended to include, but not be limited to folded sheets, multiple strips of material, loose or bonded fibers, multiple layers or laminates of such material, or other variations and combinations of such structures.

The absorbent strip 46 may be joined to the topsheet 38 (or it may be joined to any optional secondary topsheet or other optional layer positioned between the topsheet 38 and the absorbent strip 46). Alternatively, the absorbent strip 46 may be unattached to the topsheet. Preferably, however, the absorbent strip 46 is in close contact with or attached to the topsheet 38 or other overlying component. This will facilitate the transport of bodily exudates through the topsheet 38 (i.e., will draw exudates through the topsheet) due to the higher capillarity of the absorbent strip 46. The absorbent strip 46 can be joined to the overlying component in any suitable manner, including but not limited to by adhesives, heat and/or pressure bonds, meltblowing, ultrasonic bonds, extruding it onto the overlying component, or any of the other manners described in Section 2G below.

Preferably, if the absorbent strip 46 is joined to the topsheet 38, it is intermittently joined to the topsheet 38 by topsheet/liquid transporting component bonds 70 located along the longitudinal side margins of the absorbent strip near the side edges 46C of the absorbent strip 46 (several examples of these bonds are shown in FIG. 1). This type of attachment provides a structure in which the bonds between the absorbent strip 46 and the topsheet 38 will not interfere with the transfer of liquids through the topsheet 38 to the absorbent strip 46. It also provides the absorbent strip 46 with greater flexibility than if, for example, the absorbent strip were bonded to the topsheet over its entire surface by adhesives. This greater flexibility provides the sanitary napkin with enhanced conformability to the wearer's body. In other embodiments (which are also shown in FIG. 1), the absorbent strip 46 can be attached to the topsheet 38 near the ends 46D of the absorbent strip 46 by topsheet/liquid transporting component end bonds 72. In a particularly preferred embodiment, the absorbent strip 46 is integrally formed onto the underside of the topsheet 38 or other overlying component.

Figure 5:
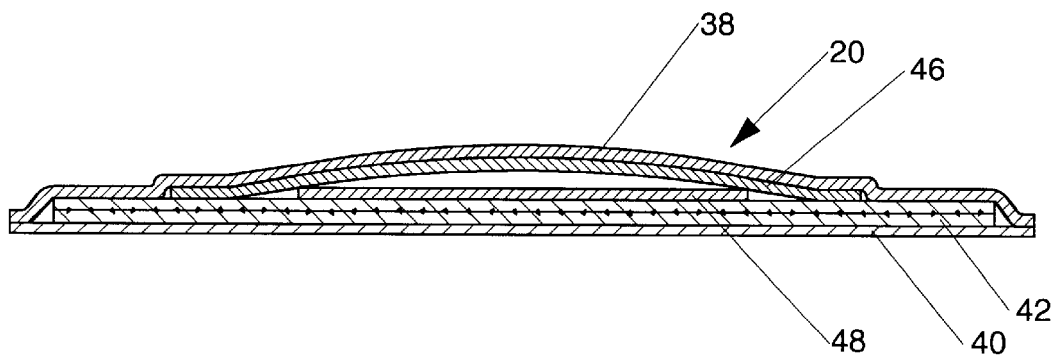
FIG. 5 is a cross-sectional view of a sanitary napkin taken from an angle similar to that of FIG. 3 in which the absorbent strip is attached only at its ends so it can "decouple" from the absorbent core.

The absorbent strip 46 may also be attached to the underlying components of the sanitary napkin. For instance, the ends 46D of the absorbent strip 46 can be attached to the absorbent core 38 by liquid transporting component/core end bonds 74. In these alternative embodiments, if the absorbent strip 46 is unattached to an underlying component between its ends, as shown in FIG. 5, the portion of the absorbent strip 46 between the areas at its ends where it is bonded can move apart from or "decouple from" the underlying component during wear to come into more intimate contact with the wearer's body. In a variation of this alternative embodiment, the absorbent strip 46 and fluid directing strip 48 can be secured to each other and the fluid directing strip 48 unattached to the underlying component (such as the absorbent core) so both the absorbent strip 46 and fluid directing strip 48 or at least portions thereof, can decouple from the absorbent core 42.

(2) The Fluid Directing Component

The fluid (that is, liquid) directing component 48, as shown in FIGS. 1–3, is a structure that is positioned between the absorbent core 42 and the absorbent strip 46.

The purpose of the fluid directing component 48 is to direct bodily fluids (i.e., liquids) such as blood, menses and urine received from the absorbent strip 46 towards the ends 42D of the absorbent core 42. The fluid directing component 48 can direct bodily discharges laterally, but it preferably does not direct such discharges all the way to the side edges 42C of the absorbent core. The fluid directing component 48 can also transport some of the bodily discharges through its thickness to the underlying absorbent core 42 (if the fluid directing component 48 is semi-pervious).

A particularly preferred fluid directing component is the fluid directing strip 48 shown in FIG. 1. The fluid directing strip 48 is a thin, flexible, liquid resistant, preferably liquid impervious strip of material, such as polyolefinic film. The fluid directing component 48 can, however, be an element of many other materials and configurations, including non-woven materials, and is not limited to thin strips of film or other material.

The fluid directing strip 48, as shown in FIG. 1, has a rectangular configuration. FIG. 1 shows a preferred embodiment in which the width of the fluid directing strip 48 is greater than the width of the absorbent strip 46 and the length of the fluid directing strip 48 is less than the length of the absorbent strip 46. The dimensions of the absorbent core 42 are greater than those of both the absorbent strip 46 and the fluid directing strip 48. The preferred dimensions of the fluid directing strip 48 can range from between about 0.3 cm. to about 0.7 cm. wider than the absorbent strip 46 and between about 0.3 cm. and 2 cm. shorter than the absorbent strip 46. The dimensions can, as in the case of the absorbent strip, be less than or greater than these preferred dimensions as long as the relationship between the sizes and boundaries of the absorbent strip, the fluid directing strip, and the absorbent core described herein are maintained.

The fluid directing strip 48 can be impervious to liquid bodily exudates, or semi-pervious (or, in other words, semi-impervious). If the fluid directing strip 48 is semi-pervious, its degree of perviousness should be sufficiently limited that the fluid directing strip is still capable of carrying out its function of directing liquids toward the ends of the sanitary napkin. The fluid directing strip 48 can be provided with a degree of perviousness in a number of ways. The fluid directing strip 48 can, for instance, be made of a semi-pervious material. Alternatively, the fluid directing strip 48 can be comprised of a normally impervious material such as a polyethylene film that is provided with apertures. The apertures should be either of such a size or such a limited distribution that liquids are not able to proceed immediately through the fluid directing strip without being directed toward the ends of the core 42.

The fluid directing strip 48 can comprise any material suitable for the above purposes. For instance, the fluid directing strip 48 can comprise a polyolefinic film (e.g., polyethylene) that is apertured or non-apertured, or even an adhesive film that could be used to secure some of the components of the sanitary napkin together (such as to secure the absorbent strip 46 to the absorbent core 42). The fluid directing strip 48 can comprise a material similar to those materials used for the topsheet 38 or the backsheet 40.

Figure 4:
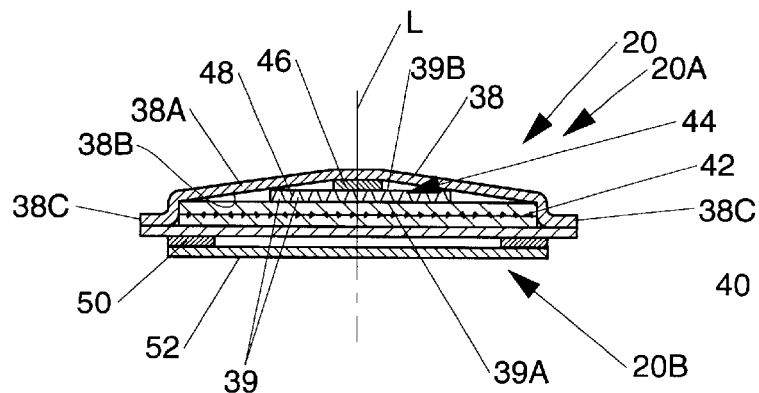
FIG. 4 is an enlarged cross-sectional view of a sanitary napkin taken from an angle similar to that of FIG. 2 which has a fluid directing strip that comprises an apertured file with tapered capillaries which is inverted so that the bottom openings of the capillaries face the topsheet of the sanitary napkin.

If the fluid directing strip 48 is comprised of a material similar to those used in the topsheet 38, however, it should typically be provided with fewer apertures or smaller apertures than would customarily be used in a topsheet. This will enable the fluid directing strip 48 to transport liquids along its surface rather than solely through its thickness. In addition, as shown in FIG. 4, the fluid directing strip 48 can comprise a material similar to one of those used for the topsheet that is provided with tapered capillaries 39 (to prevent rewet) which is then turned upside down for use as the fluid directing strip 48 so that the smaller bottom openings 39B of the capillaries face the topsheet 38.

The fluid directing strip 48 and the absorbent strip 46 can either be formed into an integral structure, joined to each other, or be unattached. If the absorbent strip 46 and the fluid directing strip 48 are joined together, they can be joined in any suitable manner. The absorbent strip 46 and the fluid directing strip 48 can be affixed by any of the means described herein which are used to secure the components of the sanitary napkin. The absorbent strip 46 and the fluid directing strip 48 may, for example, be laminated together by adhesives if the fluid directing strip comprises an adhesive film, or they may be thermally bonded if the fluid directing strip comprises a thermoplastic film. If the absorbent strip 46 and the fluid directing strip 48 are laminated together, they can be laminated together either before or during the assembly of the components of the sanitary napkin.

Preferably, if the absorbent strip 46 is joined to the fluid directing strip 48, it is intermittently joined to the fluid directing strip 48 by liquid transporting component/fluid directing component bonds 76 located along the longitudinal side margins of the absorbent strip 46 near the longitudinal side edges 46C of the absorbent strip 46. This enhances the flexibility of these components and provides a structure in which the bonds between the two components will not interfere with the transfer of liquids from the absorbent strip 46 to the fluid directing strip 48. In other embodiments, the absorbent strip 46 can be attached to the fluid directing strip 48 near the ends of the fluid directing strip 48D by liquid transporting component/fluid directing component end bonds 78.

The fluid directing strip 48 can also be formed into an integral structure with the absorbent core 42, or the fluid directing strip and the absorbent core can be joined to each other, or these two components can be unattached. If the fluid directing strip 48 is joined to the core 42, the fluid directing strip 48 can be joined to the core 42 by any of the means used to secure the components of the sanitary napkin described herein. Preferably, if the fluid directing strip 48 is joined to the core 42, it is intermittently joined to the core by fluid directing component/core side bonds 80 along the longitudinal side margins of the fluid directing strip 48 to enhance the flexibility of the sanitary napkin. Additionally or alternatively, the ends of the fluid directing strip 46 can also be attached to the absorbent core 42 by fluid directing component/core end bonds 82.

The relationship between the sizes and boundaries of the fluid directing strip 48 and the absorbent strip 46 provides the advantage that the longitudinal sides 48C of the fluid directing strip 48 extend beyond the longitudinal sides 46C of the absorbent strip 46, and the end edges 46D of the absorbent strip 46 extend beyond the end edges 48D of the fluid directing strip 48. This forces the liquid in the absorbent strip 46 to wick and be distributed to the ends of the absorbent core 42. Prior attempts did not have components with these relationships and were subject to liquids reaching the longitudinal side edges before the ends of the sanitary napkin 20. These problems were particularly evident when the prior sanitary napkins were distorted during wear.

The relationship between the component parts of the means for directional fluid distribution of the present invention is intended to remain the same even when the sanitary napkin is subjected to pressures which tend to distort the napkin during wear. The sanitary napkin will, thus, preferably continue to preferentially direct liquids toward the ends of the core even when subjected to these forces.

(3) Alternative Embodiments of the Means for Directional Fluid Distribution

There are numerous possible alternative embodiments of the means for directional fluid distribution 44 described herein. For example, the shapes of the absorbent strip 46 and the fluid directing strip 48 can be varied in other embodiments. The shape of these components may be used to provide the sanitary napkin with certain fluid directing properties or to provide the sanitary napkin with particular functional, perceptual, or aesthetic characteristics.

For example, in the preferred embodiment described above, the fluid directing strip 48 is both wider and shorter than the absorbent strip 46. In this preferred embodiment, both ends of the absorbent strip 46 extend beyond the ends of the fluid directing strip 48. Some of the benefits of the means for directional fluid distribution of the present invention will, however, still be achieved even if the absorbent strip 46 extends at least to, and preferably, beyond only one end of the fluid directing strip 48. The absorbent strip 46 can have one end that extends beyond the end of the fluid directing strip 48 to allow the absorbent strip 46 to preferentially transport liquids to at least one end of the sanitary napkin. This arrangement can even be present when the length of the absorbent strip 46 is less than the length of the fluid directing strip 48 if the absorbent strip 46 is offset from the transverse centerline more toward one end of the fluid directing strip 48 than the other. Thus, the absorbent strip 46 may extend at least to, and preferably, beyond at least one end edge of the fluid directing strip 48.

The same applies to the relationship between the widths of the two components of the means for direction fluid distribution 44. That is, some of the benefits of the means for directional fluid distribution of the present invention will still be achieved even if the fluid directing strip 48 extends laterally outward to, and preferably, beyond only one longitudinal side edge of the absorbent strip 46. The fluid directing strip may extend beyond one longitudinal side edge of the absorbent strip 46 even when the absorbent strip 46 is wider than the fluid directing strip 48, if the fluid directing strip is offset from the longitudinal centerline more toward one side of the absorbent strip 46 than the other.

Figure 6:
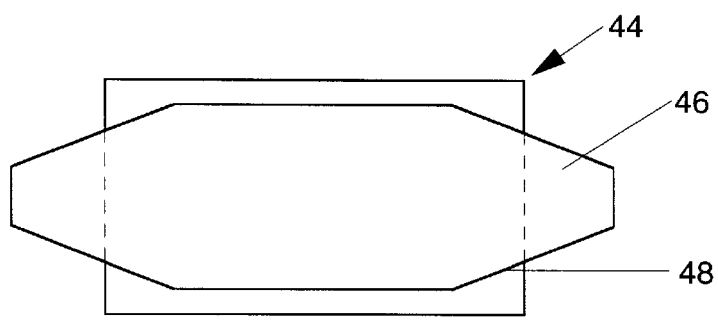
FIG. 6 is a plan view of a means for directional fluid distribution that comprises a diamond-shaped absorbent strip and a rectangular fluid directing strip.

In another example, as shown in FIG. 6, the absorbent strip 46 can comprise a diamond-shaped polygon. The absorbent strip 46 shown in FIG. 6 can be used to attempt to create essentially a single point introduction of liquids into the absorbent core 42 at the ends of the absorbent strip 46. This may be used in an attempt to acquire more control over the distribution of exudates and, thus, the soiling pattern in the sanitary napkin.

Figure 7:
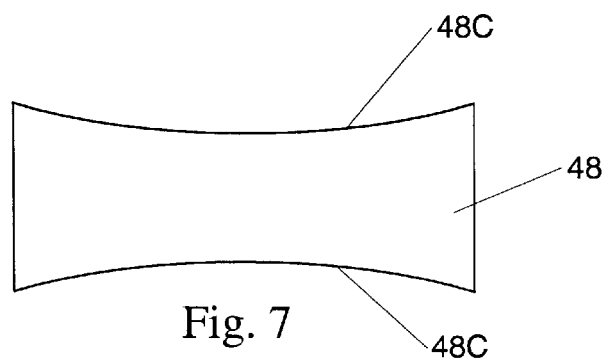
FIG. 7 is a plan view of a fluid directing strip that has concave longitudinal side edges.

FIG. 7 shows an example of a fluid directing strip 48 having concave longitudinal side edges. A fluid directing strip 48 having this shape can be used for improved wearer comfort (such as to provide room for the wearer's thighs), allowing controlled bending of the sanitary napkin at these longitudinal edges while preventing bunching of the sanitary napkin.

Figure 8:
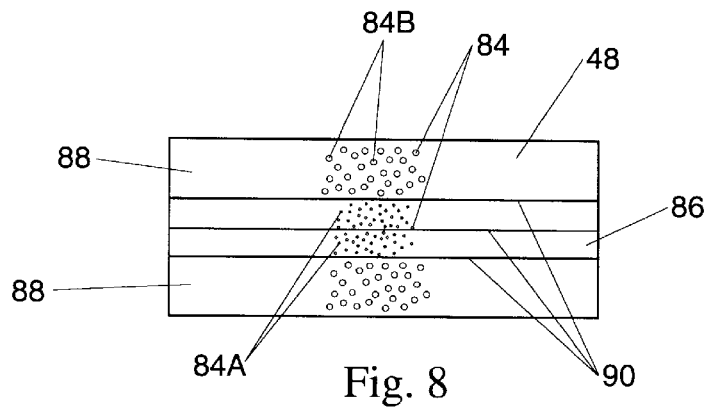
FIG. 8 is a plan view of a fluid directing strip that comprises film which has zones provided with apertures of different sizes.

FIG. 8 shows that in other alternative embodiments, the aperturing of the fluid directing strip 48 may also be used to provide the sanitary napkin with specific fluid directing properties. For example, as shown in FIG. 8, the fluid directing strip 48 may have different regions that are provided with apertures of different sizes. The fluid directing strip 48 shown in FIG. 8 has a central region 86 that may correspond to the location of the overlying absorbent strip 46 and side regions 88 that lie laterally outboard of the side edges 46C of the absorbent strip 46. The central region 86 can be provided with smaller apertures 84A (or fewer apertures per area) than the side regions 88 of the fluid directing strip. Such a structure can be used to vary the distribution of liquids to different portions of the absorbent core 42. In alternative embodiments, the apertures 84 in the fluid directing strip 48 may be of numerous different shapes.

FIG. 8 also shows that the fluid directing strip 48 may be provided with bending axes 90 to assist the means for directional fluid distribution 44 in assuming certain configurations when the sanitary napkin 20 is worn. The bending axes 90 may be formed by fold lines, score lines, densification lines, stitching lines, or any other means known in the art for providing an absorbent article with bending axes.

Figure 9:
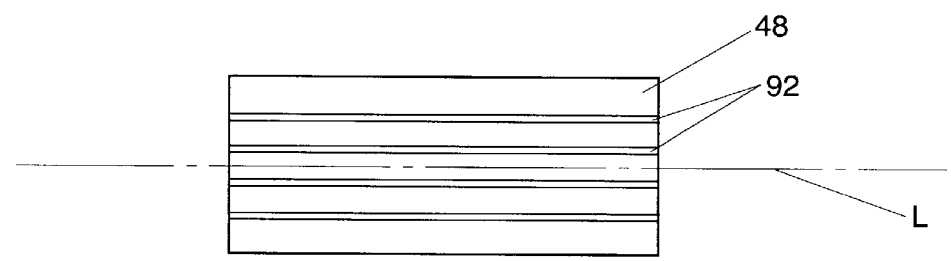
FIG. 9 is a plan view of a fluid directing strip that comprises foam which has longitudinally-oriented embossed lines formed therein.

FIG. 9 shows that the fluid directing strip 48 may additionally be embossed or otherwise provided with channels 92 for directing liquids in a particular direction, such as toward the ends of the absorbent core. In one preferred embodiment, the fluid directing strip 48 comprises a soft foam piece that is embossed with a plurality of longitudinal channels 92. Additionally, or alternatively, the fibers or other structural elements comprising the absorbent strip 46 or the fluid directing strip 48 may be oriented in a particular manner (such as in the longitudinal direction) to facilitate wicking of liquids in the longitudinal direction.

Figure 10:
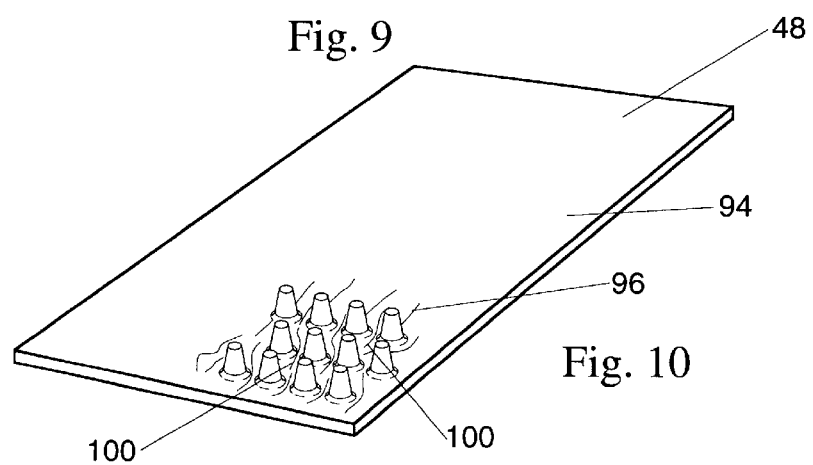
FIG. 10 is a perspective view of a fluid directing strip that comprises a flexible, hydrophobic three dimensional apertured formed film with a hydrophilic component dispersed thereon (only a portion of the apertures are shown).

FIG. 10 shows another preferred embodiment of the fluid directing strip 48. The fluid directing strip 48 is a hydrophobic structure such as a flexible, hydrophobic formed film structure 94, preferably a three dimensional apertured film, with a hydrophilic component 96 such as fibers or a surfactant dispersed thereon. The hydrophobic formed film structure 94 provides an interconnecting network 100 comprising a plurality of bucket-line structures that have to be filled up before overflowing to the core or before liquids flow toward the ends of the absorbent core.

Figure 11:
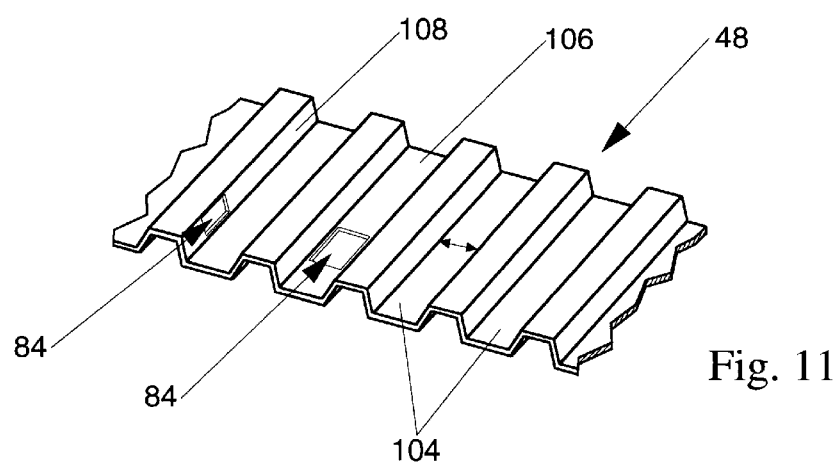
FIG. 11 is an enlarged perspective view of a fluid directing component that comprises a plastic film formed with a plurality of troughs therein.

FIG. 11 shows that in still another alternative embodiment, the fluid directing component 48 may comprise a structure such as a plastic film formed with a plurality of troughs 104 therein. Preferably, the bases 106 of the troughs 104 are less than or equal to about 100 mils (about 2.54 mm) wide to assist in the flow of menses. The structure shown in FIG. 11 can be provided with apertures 84 on the sides 108 of the troughs 104, the bases 106 of the troughs, or both. The cross-sectional shape of the troughs 104 is not limited to the shape shown in FIG. 11. The cross-section of the troughs 104 can be of any suitable configuration. The structure shown in FIG. 11 can also be used to provide the sanitary napkin with bending axes, and/or a degree of resilience, or lateral stability, or both.

In one especially preferred alternative embodiment (which will be discussed with reference to FIG. 1), the absorbent strip 46 comprises a low density material to provide the liquid transporting component with greater acquisition capabilities. The term "low density", as used herein, refers to materials having a density less than or equal to about 0.1 g/cc, and more preferably less than or equal to the following amounts: 0.09 g/cc, 0.08 g/cc, 0.07 g/cc, 0.06 g/cc, and 0.05 g/cc. Such low density materials will, however, typically sacrifice liquid distribution capabilities in comparison to higher density materials because of their lower capillarity. Materials having such low densities are typically most beneficial when they have relatively high calipers. This preferred embodiment is able to function, however, even when low caliper low density materials are used for the absorbent strip to make thin or "ultra-thin" product because the liquid distribution function of the means for directional fluid distribution can be separately handled by the fluid directing strip 48.

In alternative embodiments of this especially preferred embodiment, the absorbent strip 46 need not be used with a liquid impervious fluid directing strip 48. For instance, the absorbent strip can be used in conjunction with a fluid directing strip 48 having a higher density. Any suitable combination of these components can be used provided there is a density differential between the absorbent strip 46 and the fluid directing strip 48. This allows a liquid pervious strip to be used for the fluid directing strip 48. Such a combination has the advantage that it will preferentially distribute liquid exudates toward the ends of the absorbent core with the fluid directing strip 48 only causing limited interference with the penetration of exudates into the core.

In other alternative embodiments, the absorbent strip 46 and fluid directing strip 48 can be replaced by a means for directional fluid distribution 44 that comprises a single component. In such an alternative embodiment, the liquid transporting component and fluid directing component are integral components (i.e., portions or features) of a single component means for directional fluid distribution 44 (rather than two separate components).

Several non-limiting examples of such single component means for directional fluid distribution are described below. The single component means for directional fluid distribution can be similar in appearance to any of the means for directional fluid distribution shown in the drawings. However, the single component will typically comprise a structure in the form of a single layer with different regions that serve the various functions of the means for directional fluid distribution rather than in the for of a separate liquid transporting component placed on top of a liquid directing component.

The single component means for directional fluid distribution 44 can, for example, comprise a perforated film like one of the films specified as being useful as a topsheet. This perforated film is rendered hydrophilic by the incorporation of a surfactant (e.g., 1% Brij 76 formerly available from ICI Americas Company of Wilmington, Del.) and oriented with the cones (i.e., capillaries) facing toward the topsheet similar to the arrangement shown in FIG. 4. This will provide an impervious or semi-pervious component that is capable of transporting liquids on its surface. In variations of this embodiment, selected portions of the means for directional fluid distribution 44 can be rendered more or less hydrophilic than other portions thereof. For example, a central strip of the film similar to the central region 86 of the fluid directing strip shown in FIG. 8 can be made more hydrophilic than the regions laterally outboard of the central region, side regions 88, by applying a surfactant thereon to wick liquids along this central region.

In another preferred single component embodiment, the functions of both the absorbent strip and fluid directing strip can be carried out by a porous fibrous structure (or fibrous web) in which the finish on the fibers is varied to provide at least two regions of different hydrophilicity. These regions preferably comprise a first region, such as a fluid directing region, and an adjacent second, non-fluid directing (or less hydrophilic), region. These respective regions can be regions of a nonwoven material that have configurations resembling the central region 86 and the side regions 88 shown in FIG. 8, without the different sized apertures (or these regions could resemble various other structures shown herein).

The term "hydrophilic", as used herein, describes surfaces which are wetted by the liquid in question. The wetting of materials is generally defined in terms of contact angles and the surface tension of the liquids and solids involved. These properties are discussed in greater detail in The American Chemical Society Publication entitled, "Contact Angle, Wettability, and Adhesion", edited by Robert F. Gould and copyrighted in 1964, and in the following TRI/Princeton Publications edited by Dr. H. G. Heilweil, Publication Number 459 entitled "A Microtechnique for Determining Surface Tension" published in April 1992, and in Publication Number 468 entitled "Determining Contact Angles Within Porous Networks" published in January 1993, which are incorporated by reference herein.

The fibrous material can be a single layer fibrous web that has been produced using known processes. Typically, such processes could be carded or spunbond nonwoven processes, or a combination thereof. The fibrous structure preferably has average wet pore radii between about 40 microns and about 180 microns. A suitable method for determining pore size of fibrous structures is described in TRI/Princeton of Princeton, N.J. Publication Number 464 entitled "Automated Determination of Pore Volume Distributions and Related Properties" edited by Dr. H. G. Heilweil published in September 1992, which publication is incorporated by reference herein. The fibers of such material preferably have a denier of between about 0.1 and about 6 dpf. The fibrous structure can be made of natural or synthetic fibers.

In a fibrous structure that is made with synthetic fibers, the different regions can be provided by rendering the contact angle (specifically, the advancing contact angle) of the layer about 86 degrees to about 89 degrees in the overall structure except in the region used for directing liquids. In the region used for directing fluids, the material is subjected to another hydrophilic treatment (such as by treating it with additional surfactant) to further reduce the advancing contact angle to as low as 55 degrees. One way to achieve this is by coating the fibers of the material in the fluid directing region with a semi-durable hydrophilic surfactant such as Silwet available from ICI (Middlesbrough, U.K.).

If a cellulose base material is chosen for this latter single component execution, the starting material typically has a contact angle of between about 30 degrees and about 55 degrees. The distinct regions are preferably created in the cellulose material by coating the non-fluid directing area with a partially hydrophobic surfactant that raises the advancing contact angle of the non-fluid directing region to about 80–89 degrees. A suitable surfactant for use in such an embodiment is SCOTCHBAN L12053 available from 3M of Minneapolis, Minn.

It should be understood, however, that this embodiment of the present invention is not limited to structures having the particular contact angles within the different regions described above. This is particularly true since the effect of the contact angle is dependent upon the liquid in issue. This embodiment of the present invention will function if there is a difference in hydrophilicity between the liquid directing region and the non-liquid directing region(s). This difference in hydrophilicity is preferably established so that: (1) the advancing contact angle of the liquid directing region is less than or equal to 89 degrees; and, (2) the advancing contact angle of the non-liquid directing region(s) is greater than or equal to 10 degrees more than the advancing contact angle of the liquid directing region.

The function of these structures can be described in the following manner with reference to the regions of the structure shown in FIG. 8. In this embodiment, the central fluid directing region 86 has a lower contact angle than the adjacent side regions 88. The difference in contact angles between these regions will reduce the tendency for liquids to flow laterally from the central region 86 into the side regions 88. This will facilitate the flow of liquids in the longitudinal direction through the fluid directing region 86 since the liquids will not have anywhere else to move. The liquids can flow on the surface of the central fluid directing region 86, or between the surfaces of fluid directing region (i.e., through the thickness of the fluid directing region). Another place liquids can flow in the central fluid directing region 86 is along any basal interface below the central fluid directing region 86 and the material or layer that lies beneath the central fluid directing region.

E. The Backsheet

The backsheet 40 prevents the exudates absorbed and contained in the absorbent core 42 from wetting articles which contact the sanitary napkin 20 such as pants, pajamas and undergarments. The backsheet 40 is impervious to liquids (e.g., menses and/or urine). The backsheet 40 is preferably manufactured from a thin plastic film, although other flexible liquid impervious materials may also be used.

The backsheet 40 may comprise a woven or nonwoven material, polymeric films such as thermoplastic films of polyethylene or polypropylene, or composite materials such as a film-coated nonwoven material. Preferably, the backsheet 40 is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Tredegar Film Products of Terre Haute, Ind., under the designation XP-39385.

The backsheet 40 is preferably embossed and/or matte finished to provide a more clothlike appearance. Further, the backsheet 40 may permit vapors to escape from the absorbent core 42 (i.e., the backsheet 40 may be breathable) while still preventing exudates from passing through the backsheet 40. Flushable or biodegradable backsheets can also be used, e.g., such as with the pantiliner devices described herein.

F. Fasteners for Attaching the Sanitary Napkin to the Wearer's Panties

The outwardly-oriented face of the backsheet 40 may, as shown in FIG. 2, further comprise a means for attaching the sanitary napkin 20 to the undergarment of the wearer (such as a fastener) 50.

Fasteners comprising adhesives have been found to work well for this purpose. Any adhesive or glue used in the art for such purposes can be used, with pressure-sensitive adhesives being preferred. Suitable adhesives are Century A-305-IV manufactured by the Century Adhesives Corporation, Instant Lock 34-2823 manufactured by the National Starch Company, 3 Sigma 3153 manufactured by 3 Sigma, and Fuller H-2238ZP manufactured by the H. B. Fuller Co. Suitable adhesive fasteners are also described in U.S. Pat. No. 4,917,697.

The fastener 50 can be in many possible configurations depending on the characteristics desired for the sanitary napkin. FIG. 2 shows one preferred arrangement which utilizes two longitudinally oriented strips of adhesive, one on each side of the longitudinal centerline L. Particularly suitable fastener configurations are shown in PCT International Patent Publication No. WO 92/04000 entitled "Shape and Adhesive Fastening Means for an Absorbent Article" published in the name of Papa, et al. on Mar. 19, 1992, and in the Capillary Channel Fiber patent applications, the Curved Bun patent applications, and the Stretchable Absorbent Article patent application described in greater detail in Section 2H below.

In addition, other types of fasteners can be used instead of, or in addition to adhesives. These other types of fasteners are preferably arranged in patterns similar to those in the patent publications referred to above. Such fasteners include, but are not limited to conventional VELCRO hook material, the fasteners described in: U.S. Pat. No. 4,946,527 issued to Battrell on Aug. 7, 1990; U.S. Pat. Nos. 5,058,247 and 5,116,563 issued to Thomas, et al. on Oct. 22, 1991 and May 26, 1992, respectively; and EPO Patent Application Publication No. 0 381 087 published Aug. 8, 1990; or, high coefficient of friction foams and other high coefficient of friction materials in the same category as those described in U.S. Pat. No. 4,166,464 issued to Korpman, U.S. Pat. No. 4,834,739 issued to Linker, III, et al., and U.S. Pat. No. 5,011,480 issued to Gossens, et al.

Before the sanitary napkin 20 is placed in use, if an adhesive fastener is used, the adhesive is typically covered with a removable cover strip or release liner 52 in order to keep the adhesive from sticking to a surface other than the crotch portion of the panty prior to use. Suitable release liners are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/0, both of which are manufactured by the Akrosil Corporation.

In one particularly preferred embodiment, the adhesive fastener 50 is protected with a wrapper that not only covers the adhesive, but also provides both an individually packaged sanitary napkin and a container for disposing the sanitary napkin after use, such as is described in U.S. Pat. No. 4,556,146 issued to Swanson, et al. on Dec. 3, 1985.

The sanitary napkin 20 of the present invention is used by removing any release liner 52 and thereafter placing the sanitary napkin 20 in a panty so that the adhesive (or other fastener) 50 contacts the panty and maintains the sanitary napkin in position within the panty during use.

G. Assembly of the Components of the Sanitary Napkin

The components of the sanitary napkin such as the topsheet, the backsheet, the absorbent core, and any other components, may be assembled in a variety of well known configurations (including so called "tube" products or side flap products).

The components of the sanitary napkin are preferably assembled in a "sandwich" configuration with the topsheet, backsheet, and absorbent core each comprising a layer and the absorbent core positioned between the topsheet and backsheet. The topsheet 38 and the backsheet 40 are preferably peripherally joined using known techniques. The topsheet 38 and backsheet 40 can be joined either entirely peripherally so that the entire perimeter of the sanitary napkin 20 is circumscribed by the joinder of the components, or these two components can be only partially peripherally joined at the perimeter.

The components of the sanitary napkin 20 can be secured together by adhesives, stitching, heat and/or pressure bonds, dynamic mechanical bonds, ultrasonic bonds, intermingling or entanglement of the fibers or other structural elements comprising the components of the sanitary napkin, such as by meltblowing the fibers comprising one component onto another component, extruding one component onto another, or by any other means known in the art. Suitable means for attaching the components of the sanitary napkin are described in the patent applications described above filed in the name of Cree, et al.

H. Alternative Embodiments and Optional Features

The sanitary napkin 20 may also be provided with a pair of flaps, each of which are adjacent to and extend laterally outward from a side edge of the main body portion of the sanitary napkin. (The main body portion is the portion of the sanitary napkin without the flaps.) The flaps are preferably configured to drape over the edges of the wearer's panties in the crotch region so that they are disposed between the wearer's panties and the wearer's thighs.

Such flaps can serve at least two purposes. First, the flaps help to prevent soiling of the wearer's body and panties by menstrual fluid. Second, the flaps are preferably provided with attachment means on their garment surface so that the flaps can be folded back under the panty and attached to the garment-facing side of the panty. In this way, the flaps serve to keep the sanitary napkin 20 properly positioned in the panty. Alternatively, the flaps may be attached to each other on the underside of the panty by the attachment means with or without also being affixed to the panty.

A number of sanitary napkins having flaps suitable or adaptable for use with the sanitary napkin 20 of the present invention are known. Such flaps are disclosed in U.S. Pat. No. 4,285,343 entitled "Sanitary Napkin", issued to McNair on Aug. 25, 1981; U.S. Pat. No. 4,589,876 entitled "Sanitary Napkin", issued to Van Tilburg on May 20, 1986; U.S. Pat. No. 4,608,047 entitled "Sanitary Napkin Attachment Means", issued to Mattingly on Aug. 26, 1986; U.S. Pat. No. 4,687,478, entitled "Shaped Sanitary Napkin With Flaps", issued to Van Tilburg on Aug. 18, 1987; and in Reexamination Patent B1 4,589,876 issued Apr. 27, 1993. Some particularly preferred types of flaps are described in the following U.S. patent applications: Ser. No. 07/769,891 entitled "Absorbent Article Having Flaps and Zones of Differential Extensibility" filed in the name of Lavash, et al. on Oct. 1, 1991 (PCT Publication No. WO 93/06805, published Apr. 15, 1993); and in Ser. No. 07/906,593 entitled "Absorbent Article Having Unitary Release Material" filed in the name of Lavash, et al. and Ser. No. 07/906,629 entitled "Absorbent Article Having Tucked Flaps" filed in the name of Osborn, et al .f, both filed Jun. 30, 1992.

While p referred sanitary napkin embodiments of the present invention have been described, numerous other sanitary napkin embodiments are disclosed in the literature. These could also be provided with the means for directional fluid distribution of the present invention. Several such sanitary napkins are disclosed in U.S. Pat. No. 4,425,130, "Compound Sanitary Napkin" issued to DesMarais on Jan. 10, 1984; U.S. Pat. No. 4,321,924, "Bordered Disposable Absorbent Article" issued to Ahr on Mar. 30, 1982; the aforementioned U.S. Pat. No. 4,950,264 issued to Osborn on Aug. 21, 1990; U.S. Pat. No. 5,007,906 entitled "Decoupled Sanitary Napkin" issued to Osborn, et al. on Apr. 16, 1991; the aforementioned U.S. Pat. No. 5,009,653 issued to Osborn on Apr. 23, 1991; U.S. Pat. No. 4,917,697 entitled "Sanitary Napkin Having Flaps and Stress Relief Means" issued to Osborn et al. on Apr. 17, 1990, U.S. Pat. No. 5,171,302 entitled "Absorbent Article With Central Hinge" issued to Buell on Dec. 15, 1992; U.S. Pat. No. 5,197,959 entitled "Absorbent Article" issued to Buell on Mar. 30, 1993; and in U.S. patent application Ser. No. 07/605,583 entitled, "Sanitary Napkin Having Components Capable of Separation in Uses" filed in the name of Visscher, et al. on Oct. 29, 1990 (PCT Publication No. WO 92/07537, published May 14, 1992); U.S. patent application Ser. No. 07/630,451 entitled "Sanitary Napkin Having Transversely Segmented Core" filed in the name of Osborn et al. on Dec. 19, 1990 (PCT Publication No. 92 WO/10984, published Jul. 9, 1992); U.S. patent application Ser. No. 07/707,233 entitled "Sanitary Napkin Having Laterally Extensible Means for Attachment to the Undergarment of the Wearer", filed May 21, 1991 in the name of Osborn et al. (EPO Application No. 90202826.5); and in U.S. patent application Ser. No. 07/874,872 entitled "Generally Thin, Flexible Sanitary Napkin Having Stiffened Center" filed in the name of Osborn on Apr. 28, 1992.

The sanitary napkin described herein can be comprised one or more extensible components. In one preferred embodiment, most or all of the components are extensible to provide a degree of extensibility (on the order of 15%–40%) to the absorbent article. This extensibility may provide better in-use fit and comfort. In a particularly preferred alternative embodiment, the sanitary napkin 20 is comprised of components that are extensible (preferably, capable of stretching), particularly in the longitudinal direction when the sanitary napkin Is worn. Suitable extensible absorbent articles are described in U.S. patent application Ser. No. 07/915,133 entitled "Stretchable Absorbent Articles" filed in the name of Osborn, et al. on Jul. 23, 1992 (PCT Publication No. WO 93/01785 published Feb. 4, 1993).

In addition, other sanitary napkins that may be provided with the means for directional fluid distribution of the present invention are described in the following pending U.S. Patent Applications which were filed on Jul. 23, 1992: U.S. patent application Ser. No. 07/915,202, entitled "Curved, Shaped Absorbent Article" filed in the name of Theresa L. Johnson, et al. (PCT Publication No. WO 93/01781); U.S. patent application Ser. No. 07/915,285, entitled "Absorbent Article Having Resilient Center" filed in the name of Thomas W. Osborn, et al. (PCT Publication No. WO 93/01782); U.S. patent application Ser. No. 07/915,201, entitled "Absorbent Article Fastener Pattern" filed in the name of Robb E. Olsen, et al. (PCT Publication No. WO 93/01783); and, U.S. patent application Ser. No. 07/915,134, entitled "Method of Making Curved, Shaped Absorbent Article" filed in the name of Letha M. Hines, et al. (PCT Publication No. 10 93/01784).

The terms "panty liner" or "pantiliner" refer to absorbent articles that are less bulky than sanitary napkins which are generally worn by women between their menstrual periods. Suitable absorbent articles in the form of pantiliners which could be provided with the means for directional fluid distribution of the present invention are disclosed in U.S. Pat. No. 4,738,676 entitled "Pantiliner" issued to Osborn on Apr. 19, 1988.

The term "incontinence article" refers to pads, undergarments (pads held in place by a suspension system of same type, such as a belt, or the like), inserts for absorbent articles, capacity boosters for absorbent articles, briefs, bed pads, and the like, regardless of whether they are worn by adults or other incontinent persons. Suitable incontinence articles that can be provided with the means for directional fluid distribution described herein are disclosed in U.S. Pat. No. 4,253,461 issued to Strickland, et al. on Mar. 3, 1981; U.S. Pat. Nos. 4,597,760 and 4,597,761 issued to Buell; U.S. Pat. No. 4,704,115; U.S. Pat. No. 4,909,802 issued to Ahr, et al.; U.S. Pat. No. 4,964,860 issued to Gipson, et al. on Oct. 23, 1990; and in U.S. patent application Ser. NOS. 07/637,090 and 07/637,571 filed respectively by Noel, et al. and Feist, et al. on Jan. 3, 1991 (PCT Publication No. WO 92/11830 entitled "Absorbent Article Having Rapid Acquiring, Multiple Layer Absorbent Core" published in the name of Noel, et al. and PCT Publication No. WO 92/11831 entitled "Absorbent Article Having Rapid Acquiring, Wrapped Multiple Layer Absorbent Body" published in the name of Feist, et al., both published on Jul. 23, 1992).

The focus of the present invention is on absorbent articles that are intended to be worn in the crotch region of the wearer's undergarments. However, the features of the present invention could also be used in absorbent articles such as diapers. Diapers are absorbent articles worn by infants and incontinent persons that are fastened about the waist of the wearer. Suitable diapers that can be provided with the means for directional fluid distribution of the present invention are disclosed in U.S. Pat. No. 3,860,003 issued to Buell on Jan. 14, 1975, and U.S. Pat. No. 5,151,092 issued to Buell, et al. on Sep. 29, 1992.

Figure 12:
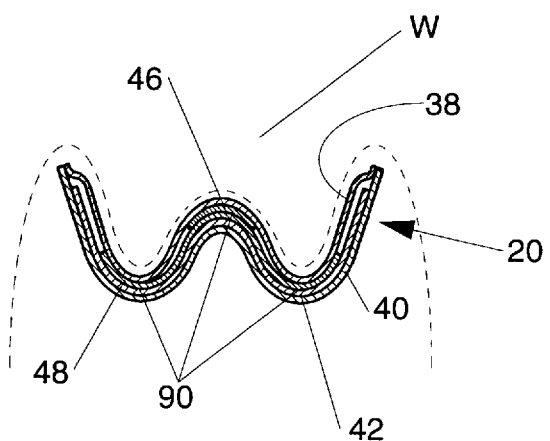
FIG. 12 is a simplified schematic cross-sectional view which shows how the sanitary napkin preferably fits adjacent to the wearer's body in a "W" shape.
Figure 13:
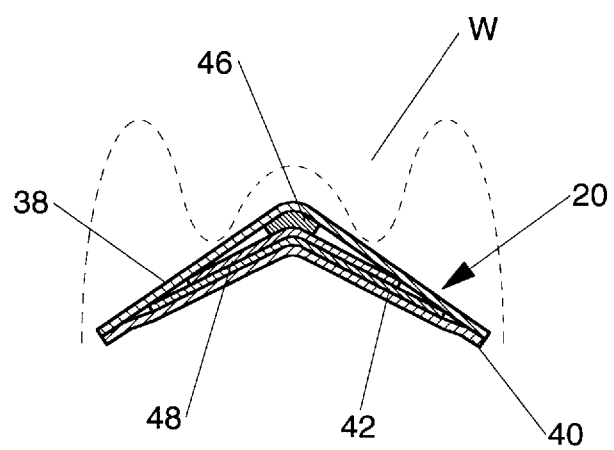
FIG. 13 is a simplified schematic cross-sectional view which shows how the sanitary napkin preferably fits adjacent to the wearer's body in an inverted "V" shape.

I. Flexibility of the Sanitary Napkin and Configurations the Sanitary Napkin May Take When Worn The components of the means for directional fluid distribution 44 have the specific relationships between their lengths and widths described herein, and are sufficiently flexible and joined in such a way that they maintain the desired relationships with each other during wear, particularly when the sanitary napkin 20 is laterally compressed. FIGS. 1, 12, and 13 show how this is accomplished.

FIG. 1 shows that the absorbent strip 46 and the fluid directing strip 48 lie along the longitudinal centerline of the sanitary napkin 20. The absorbent strip 46 and the fluid directing strip 48, being additional layers, provide the sanitary napkin with a stiffened region along the longitudinal centerline of the sanitary napkin 20 (i.e., a longitudinal central region 34). The longitudinal central region 34, in other words, is stiffer than the surrounding longitudinal side regions 36.

The flexibility of the various regions of the sanitary napkin is expressed in terms of flexure-resistance. The flexibility is measured according to the Circular Bend Procedure (described In greater detail below). The longitudinal central region 34 preferably has a flexure-resistance of up to: less than or equal to about 1,000 grams, more preferably less than or equal to about 700 grams, even more preferably less than or equal to about 500 grams, and most preferably less than or equal to about 400 grams. The surrounding longitudinal side regions 36 preferably have flexure resistances that are less than that of the longitudinal central region 34 and less than or equal to about 700 grams, more preferably less than or equal to about 600 grams, more preferably less than or equal to about 500 grams, more preferably less than or equal to about 400 grams, more preferably less than or equal to about 300 grams, and most preferably less than or equal to about 250 grams. The flexure-resistance of the longitudinal side regions 36 may also be any of those figures specified for the sanitary napkin described in U.S. Pat. No. 5,009,653 issued to Osborn.

The flexure-resistance of the different regions of the sanitary napkin is measured as peak bending stiffness. Peak bending stiffness is determined by a test which is modeled after the ASTM D 4032-82 Circular Bend Procedure. The ASTM procedure is modified for use herein. The Circular Bend Procedure as modified and used for the purposes of the present invention is hereinafter simply referred to as the "Circular Bend Procedure". One version of the Circular Bend Procedure is described in U.S. Pat. No. 5,009,653 issued to Osborn. The Circular Bend Procedure is a simultaneous multi-directional deformation of a material in which one face of a specimen becomes concave and the other face becomes convex. The Circular Bend Procedure gives a force value related to flexure-resistance, simultaneously averaging stiffness in all directions.

In the case of the present invention when carrying out the Circular Bend Procedure, rather than using one set of samples taken from the sanitary napkins as described in U.S. Pat. No. 5,009,653, separate samples are taken from longitudinal central region 34 and from the longitudinal side regions 36 of the sanitary napkins. The samples are tested and averaged separately so a flexure-resistance value is obtained for the longitudinal central region 34, and a separate value is obtained for the surrounding regions 36.

APPARATUS

The apparatus necessary for the CIRCULAR BEND PROCEDURE is a modified Circular Bend Stiffness Tester, having the following parts:

A smooth-polished steel plate platform which is 102.0× 102.0×6.35 millimeters having an 18.75 millimeter diameter orifice. The lap edge of the orifice should be at a 45 degree angle to a depth of 4.75 millimeters.

A plunger having an overall length of 72.2 millimeters, a diameter of 6.25 millimeters, a ball nose having a radius of 2.97 millimeters and a needle-point extending 0.88 millimeter therefrom having a 0.33 millimeter base diameter and a point having a radius of less than 0.5 millimeter, the plunger being mounted concentric with the orifice and having equal clearance on all sides. Note that the needle-point is merely to prevent lateral movement of the test specimen during testing. Therefore, if the needle-point significantly adversely affects the test specimen (for example, punctures an inflatable structure), then the needle-point should not be used. The bottom of the plunger should be set well above the top of the orifice plate. From this position, the downward stroke of the ball nose is to the exact bottom of the plate orifice.

A force-measurement gauge and more specifically an Instron inverted compression load cell. The load cell has a load range of from about 0.0 to about 2000.0 grams.

An actuator, and more specifically the Instron Model No. 1122 having an inverted compression load cell. The Instron 1122 is made by the Instron Engineering Corporation, Canton, Mass.

NUMBER AND PREPARATION OF SPECIMENS

In order to perform the procedure for this test, as explained below, five representative sanitary napkins are necessary. From one of the five napkins to be tested, some number "Y" of 37.5×37.5 millimeter test specimens are cut. At least one specimen is cut from the portion of the sanitary napkin containing any means for directional liquid distribution (such as along the longitudinal centerline of the sanitary napkin), and at least one specimen is cut from the adjacent regions of the sanitary napkin that are outboard of any means for directional liquid distribution. If due to the plan view shape of the region to be tested, it is not possible to cut a square 37.5×37.5 mm. specimen, any other 1,400 square millimeter size specimen may be used, provided the specimen adequately covers the orifice in the test platform to properly carry out the test.

Specimens having portions in which a topsheet is joined directly to a barrier sheet or which are a laminate of a topsheet and a barrier sheet, should also not be tested. The reason that these specimens are not tested is due to the realization that prior art napkins exist in which a topsheet is joined to a barrier sheet beyond the edges of an absorbent core in the periphery of the napkin, such portions of which are highly flexible. The present invention is more concerned with the flexibility of the significant absorbent portions of the sanitary napkin. If any of the significant absorbent portions of the sanitary napkin meet the parameters set forth in the appended claims for the particular regions, then the sanitary napkin falls within the scope of the appended claims. A number of different specimens should be tested from each sanitary napkin. In particular, the structurally least flexible portions in the center of the sanitary napkin should be tested as the longitudinal central region. The most flexible portions of the sanitary napkin should be tested when samples of the longitudinal side regions of the napkin are measured.

The test specimens should not be folded, bent, or compressed by the test person, and the handling of specimens must be kept to a minimum and to the edges to avoid affecting flexural-resistance properties. From the four remaining sanitary napkins, an equal number "Y" of specimens, identical to the specimens cut from the first napkin, are cut. Thus, the test person should have "Y" number of sets of five identical specimens.

PROCEDURE

The procedure for the CIRCULAR BEND PROCEDURE is as follows. The specimens are conditioned by leaving them in a room which is 21±1° C. and 50±2% relative humidity for a period of two hours. The test plate is leveled. The plunger speed is set at 50.0 centimeters per minute per full stroke length. A specimen is centered on the orifice platform below the plunger such that the body surface 20A of the specimen is facing the plunger and the garment surface 20B of the specimen is facing the platform with the release paper removed from any adhesive on the garment surface of the specimen and the adhesive sprinkled with corn starch to eliminate the adhesive tack. The indicator zero is checked and adjusted, if necessary. The plunger is actuated. Touching the specimen during the testing should be avoided. The maximum force reading to the nearest gram is recorded. The above steps are repeated until all five of the identical specimens have been tested.

CALCULATIONS

The peak bending stiffness for each specimen is the maximum force reading for that specimen. Each set of five identical specimens is tested and the five values received for that set are averaged. Thus, the test person now has an average value for each of the "Y" identical sets of specimens tested. If any of the significant absorbent portions of the sanitary napkin have a longitudinal central region and surrounding regions with average for each identical specimen with the requisite flexure-resistances, then the napkin satisfies the parameters of this test.

FIGS. 12 and 13 are simplified schematic cross-sectional views which show two possible configurations that the sanitary napkin 20 of the present invention may take when worn. The means for directional fluid distribution 44 provides the sanitary napkin 20 with a stiffer longitudinal central region 34 that may bend as indicated, but does not "rope" or distort in such an amount as to interfere with the fluid directing function of the means for directional fluid distribution 44.

FIG. 12 shows an embodiment in which the sanitary napkin fits adjacent to the wearer's body (particularly the insides of the upper portions of the wearer's thighs and the wearer's labia majora) in a "W" shape. (The wearer's body is designated "W" in the drawings.) FIG. 12 also shows how the optional bending axes 90 provided in the sanitary napkin 20 can be used to assist the sanitary napkin in assuming the desired in-use cross-sectional configuration. If the fluid directing strip 48 comprises a thin strip of film, it is typically flexible enough that the sanitary napkin can assume such a configuration even without providing the fluid directing strip 48 with such bending axes, however.

FIG. 13 shows an embodiment in which the sanitary napkin fits adjacent to the wearer's body (particularly the insides of the upper portions of the wearer's thighs and the wearer's labia majora) in an inverted "V" shape.

In alternative embodiments, the sanitary napkin 20 of the present invention may assume any of the other different configurations in the above-referenced U.S. patent application Ser. No. 07/832,797, entitled "Sanitary Napkin With Stiffened Center" filed in the name of Osborn on Jan. 22, 1993.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

While particular embodiments of the present invention have been illustrated and described, it would be obvious to those skilled in the art that various other changes and modifications can be made without departing from the spirit and scope of the invention.

What is claimed is:

1. A sanitary napkin comprising:
   a liquid pervious topsheet;
   a liquid impervious backsheet joined to said topsheet;
   an absorbent core having a length, a width, and a pair of end edges positioned between said topsheet and said backsheet;
   a liquid transporting component positioned between said topsheet and said absorbent core, said liquid transporting component having a length, a width, a pair of side edges, and a pair of end edges wherein the length of said liquid transporting component is less than the length of said absorbent core; and
   a liquid directing component for directing liquid exudates toward the end edges of said absorbent core by controlling the flow of the liquid exudates being transported by said liquid transporting component into said absorbent core, said liquid directing component being positioned between said liquid transporting component and said absorbent core, said liquid directing component having a length, a width, a pair of side edges, and a pair of end edges, wherein:
      at least one of the end edges of said liquid transporting component extends beyond the one of the end edges of said liquid directing component so that said liquid transporting component transports liquid exudates beyond the end edges of said liquid directing component.

2. The sanitary napkin of claim 1 wherein said liquid transporting component comprises a strip of absorbent material.

3. The sanitary napkin of claim 1 wherein said liquid transporting component comprises a laminate of two tissue layers with absorbent gelling material therebetween.

4. The sanitary napkin of claim 1 wherein both ends of said liquid transporting component extend beyond the ends of said liquid directing component, and said liquid transporting component is joined to the underlying absorbent core only at the ends of said liquid transporting component and is unattached to any underlying element between said ends to provide an unattached portion of said liquid transporting component that is capable of separating from said absorbent core when said sanitary napkin is worn.

5. The sanitary napkin of claim 1 wherein said liquid directing component is hydrophilic.

6. The sanitary napkin of claim 1 wherein said liquid directing component is hydrophobic.

7. The sanitary napkin of claim 1 wherein said liquid directing component comprises a liquid impervious structure.

8. The sanitary napkin of claim 7 wherein said liquid directing component comprises a strip of film.

9. The sanitary napkin of claim 1 wherein said sanitary napkin has a longitudinal centerline that extends in a longitudinal direction and said liquid directing component comprises a structure with a plurality of liquid directing channels extending in the longitudinal direction formed therein.

10. The sanitary napkin of claim 9 wherein said liquid directing component comprises a piece of foam.

11. The sanitary napkin of claim 9 wherein said liquid directing component comprises a strip of material having liquid directing channels with trapezoidal cross-sections.

12. The sanitary napkin of claim 11 wherein said trapezoidal-shaped channels have a base and walls, and at least one of said base and said walls have apertures provided therein.

13. The sanitary napkin of claim 1 wherein said liquid directing component comprises a semi-liquid impervious structure.

14. The sanitary napkin of claim 13 wherein said liquid directing component comprises an apertured film.

15. The sanitary napkin of claim 1 wherein both end edges of said liquid transporting component extend beyond the end edges of the liquid directing component.

16. The sanitary napkin of claim 1 wherein at least one side edge of said liquid directing component extends laterally outward beyond one of the side edges of the liquid transporting component.

17. The sanitary napkin of claim 1 wherein the width of said liquid transporting component is between about 1 cm and about 4 cm and the length of said liquid transporting component is between about 7 cm and about 15 cm.

18. The sanitary napkin of claim 1 wherein the width of said liquid directing component is between about 0.3 cm to about 0.7 cm wider than said liquid transporting component, and the length of said liquid directing component is between about 0.3 cm to about 2 cm shorter than said liquid transporting component.

19. The sanitary napkin of claim 1 wherein said liquid directing component has curved, concave inward side edges.

20. The sanitary napkin of claim 1 wherein said liquid transporting component and said liquid directing component comprise two separate elements.

* * * * *